United States Patent
Dinsmore et al.

(10) Patent No.: US 6,205,845 B1
(45) Date of Patent: Mar. 27, 2001

(54) DISC DRIVE OUTGASSING SYSTEM

(75) Inventors: Michael Paul Dinsmore, Longmont; Philip John Gooras, Frederick, both of CO (US)

(73) Assignee: Seagate Technology LLC, Scotts Valley, CA (US)

(*) Notice: Subject to any disclaimer, the term of this patent is extended or adjusted under 35 U.S.C. 154(b) by 0 days.

(21) Appl. No.: 09/318,909

(22) Filed: May 26, 1999

Related U.S. Application Data (60) Provisional application No. 60/121,153, filed on Feb. 22, 1999.

(51) Int. Cl.[7] .............................. G01N 1/00; G01N 7/14; F16K 11/22
(52) U.S. Cl. ................................. 73/37; 73/864.74; 73/52
(58) Field of Search .................................. 73/37, 1 G, 52, 73/40.7, 864.84, 864.21, 864.74, 864.87

(56) References Cited

U.S. PATENT DOCUMENTS

| | | | | |
|---|---|---|---|---|
| 2,737,803 | * | 3/1956 | Doudera, Jr. et al. | 73/37 |
| 3,719,070 | * | 3/1973 | Hanes | 73/37 |
| 4,733,555 | * | 3/1988 | Franks | 73/49.3 |
| 4,926,681 | * | 5/1990 | Fitzpatrick | 73/52 |
| 5,347,845 | * | 9/1994 | Kepler | 73/31.03 |
| 5,363,707 | | 11/1994 | Augenblick et al. | 73/864.84 |
| 5,417,105 | * | 5/1995 | Martinez et al. | 73/40.7 |
| 5,529,097 | * | 6/1996 | Campbell | 141/51 |
| 5,553,483 | * | 9/1996 | Armentrout et al. | 73/40 |
| 5,646,334 | | 7/1997 | Scheppers et al. | 73/1.06 |
| 5,708,219 | | 1/1998 | Scheppers et al. | 73/863.31 |
| 5,728,929 | * | 3/1998 | Gevaud | 73/19.12 |
| 5,753,791 | | 5/1998 | Scheppers et al. | 73/1.06 |
| 5,773,707 | | 6/1998 | Scheppers et al. | 73/1.03 |
| 5,792,423 | | 8/1998 | Markelov | 422/83 |
| 5,859,356 | | 1/1999 | Scheppers et al. | 73/107 |
| 5,869,741 | | 2/1999 | Scheppers et al. | 73/1.06 |
| 6,050,133 | * | 4/2000 | Achter et al. | 73/40.7 |
| 6,119,534 | * | 9/2000 | Dinsmore | 73/864.91 |

* cited by examiner

*Primary Examiner*—Hezron Williams
*Assistant Examiner*—David J. Wiggins
(74) *Attorney, Agent, or Firm*—Merchant & Gould P.C.

(57) ABSTRACT

A system for collecting outgassed compounds from a disc drive includes the following structure into which the disc drive fits during such an outgassing test a base portion and a top plate connected to the base portion to move between a first and second positions to clamp a pair of valves to an outer cover of the disc drive. The two valves each include a needle plunger that may be extended from the valve to penetrate the outer cover of the disc drive and create a flow path for on inert gas sweeping between the two valves through the interior of the disc drive. An inflow line connects a source of inert gas to one valve to mix the inert gas with the outgassed compounds within the interior of the disc drive. An outflow line connects the second valve to a trap containing absorbents to separate substantially all of the outgassed compounds from the inert gas. A power supply and a disc controller operate the disc drive in a realistic manner during the course of the test.

19 Claims, 6 Drawing Sheets

DISC DRIVE OUTGASSING SYSTEM

RELATED APPLICATION

This application claims the benefit of U.S. Provisional Application 60/121,153, entitled WHOLE DRIVE OUTGASSING APPARATUS, filed Feb. 22, 1999.

FIELD OF THE INVENTION

The present invention relates to collecting chemicals and chemical compounds outgassed by a disc drive. More particularly, the present invention relates to a system for collecting outgassed compounds by passing a flow of inert gas through the disc drive housing to collect the outgassed compounds for further analysis.

BACKGROUND OF THE INVENTION

It is well known that complex electromechanical devices, such as computer disc drives, can be hanned by foreign substances which come into contact with vital components of the device. For example, dirt or dust particles which accumulate on the platters of a disc drive can damage the read/write head of the drive causing a "crash. " Thus, such devices are typically manufactured within a clean room environment and are sealed prior to leaving the clean room to reduce or prevent the possibility of such contamination.

However, the current breed of disc drives spin much faster and are more densely packed with data than prior drives. These speed and size increases require that the read/write heads fly very close to the surface of the disc platters (on the order of a micron). In light of these very low fly heights, it is possible for matter smaller than common dust or smoke particles to cause head/disc crashes. Indeed, even chemicals or chemical compounds which are outgassed by the disc drive may accumulate or be combined with other compounds to interfere with the drive heads.

Although some disc drive components outgas chemicals and chemical compounds while the drive is inactive, the level of outgassing typically increases when the drive is operating and the components are exposed to high temperatures. These outgassed chemicals and chemical compounds are easily transported throughout the drive (due to the rotation of the disc platters and the resulting air currents within the drive) where they typically bond to the substrate that coats the disc platters. In addition to physically interfering with the drive heads during operation of the drive, some outgassed compounds (e.g., adhesives) may react chemically with the drive heads during periods of inactivity when the heads are in direct contact with the disc platters. Such chemical reactions cause stiction between the heads and the disc platters which further contributes to early disc drive failure.

Thus, it is important for disc drive manufacturers to carefully monitor the outgassed compounds generated by the disc drive both in its static state,as well as during operation of the drive. The typical manner of determining the type and amount of compounds outgassed by a disc drive is to test the individual components of the disc drive. For example, each major component (or a portion thereof) may be tested by placing the component within a testing container and then sampling the interior volume of the container to determine which compounds have been outgassed during the course of the test. Such headspace sampling typically entails heating the sample container for a period of time and drawing a small sample from the sealed container. The sample is then analyzed with appropriate instrumentation, such as a gas chromatograph and a mass spectrum analyzer, to determine the composition of the outgassed compounds. Alternatively, dynamic sampling systems may be utilized in place of the above-described static sampling system to collect the compounds outgassed within the sample container. Dynamic sampling systems typically direct a flow of inert gas through the sample container and then through a trap which bonds with the outgassed compounds while allowing the inert gas to pass through the trap. One example of a dynamic system for sampling outgassed compounds from individual components is shown in U.S. Pat. No. 5,646,334 entitled MULTI-SAMPLE DYNAMIC HEADSPACE SAMPLER, issued Jul. 8, 1997 to Scheppers et al., assigned to the assignee of the present invention.

Once all of the individual disc drive components have been tested, the results may be combined and compared to a maximum or global tolerance for each identified compound. In this manner, individual disc drive components may be replaced or modified as necessary to maintain the overall outgassing levels of the disc drive below the defined maximum tolerances. However, the process of testing each disc drive component separately necessarily ignores interactions which may occur between the components as they operate together within the disc drive. Additionally, it is not possible to accurately test the contributions of some of the drive components outside of the drive itself. For example, the outgassing contributions of materials which are not fully exposed to the interior of the disc drive (e.g., pressure sensitive adhesives, gaskets, tape seals, etc.) are difficult to gauge from individual tests of those materials. Thus, individual component testing does not typically provide a true representation of the outgassing that occurs within the interior of an operative disc drive.

One solution to the problems associated with individual component testing is to pass an inert gas through the interior of the disc drive itself. Sampling the entire disc drive in this manner is typically accomplished by removing the drive top cover and replacing it with a modified cover having gas inlet and outlet ports formed therein. Gas inlet and outlet lines attached to the ports in the modified top cover then direct a flow of inert gas through the disc drive to remove any outgassed compounds for analysis. However, prior "whole drive" outgassing tests do not provide highly accurate or representative results due to the use of the modified top cover in place of the original drive top cover. For example, the modified top cover will not typically include all of the elements of a conventional top cover, such as breather filters, pressure sensitive adhesives, vibration dampeners or the original tape seal. Additionally, the original top cover typically contains absorbent filters for absorbing compounds outgassed within the disc drive. If the modified top cover does not contain these same filters then any outgassing test conducted with the modified top cover will detect unrealistically high levels of the outgassed compounds. Furthermore, the process of removing the original top cover and installing the modified top cover can lead to contamination and cause further anomalous readings.

While it is preferable to perform whole drive outgassing tests under actual operating conditions, the use of the above described modified top cover makes this process difficult, if not impossible. Because the top cover is an integral component of the disc-drive, the replacement of the original top cover with the modified top cover for the outgassing test frequently results in impaired operation or outright failure of the disc drive during the course of the test. Therefore, prior art whole drive outgassing tests are severely impaired due to the tendency of the modified top cover to both contaminate the test results and inhibit normal drive operation during the test.

In summary, regardless of whether individual disc drive components are tested separately or the entire drive is tested with a modified top cover, prior outgassing tests have not provided truly representative or accurate indications of the compounds which are outgassed within a disc drive during operation of the drive.

It is with respect to these and other background considerations, limitations and problems that the present invention has evolved.

SUMMARY OF THE INVENTION

In accordance with the present invention, a disc drive outgassing apparatus is provided for directing a flow of gas through the interior of the disc drive. The apparatus includes a base portion and a top plate connected to the base portion to move between a first position adapted to receive the disc drive and a second position adapted to clamp the disc drive between the top plate and the base portion. The top plate includes two valves attached so as to contact an outer cover of the disc drive at two separate points when the top plate is moved to the second position. The two valves (one inflow valve and one outflow valve) each include a needle plunger that may be selectively moved between a retracted position within the valve and an extended position protruding from the valve to penetrate an outer cover of the disc drive and create a flow path between the two valves through the interior of the disc drive.

The present invention further includes a system for collecting outgassed compounds from a disc drive during operation of the disc drive. The system includes a disc drive outgassing apparatus for penetrating an outer cover of the disc drive to form separate inflow and outflow openings. Separate inflow and outflow valves are attached to the disc drive to communicate with an interior of the disc drive through the respective inflow and outflow openings. An inflow line connects a source of inert gas to the inflow valve to mix the inert gas with the outgassed compounds within the interior of the disc drive. An outflow line connects the outflow valve to a trap containing absorbents for bonding with non-inert chemical compounds. A vacuum pump connected to the trap downstream of the outflow line draws the mixture of inert gas and the outgassed compounds through the outflow line to the trap to separate substantially all of the outgassed compounds from the inert gas. In one embodiment of the present invention, a power supply and a disc controller are added to the system to provide realistic operating conditions for the disc drive during the course of the outgassing test. In a still further embodiment, the disc drive outgassing apparatus is placed within an oven to maintain the disc drive at a predetermined temperature during the outgassing test.

These and various other features as well as advantages which characterize the present invention will be apparent from a reading of the following detailed description and a review of the associated drawings.

DETAILED DESCRIPTION OF THE PREFERRED EMBODIMENTS

Figure 1:
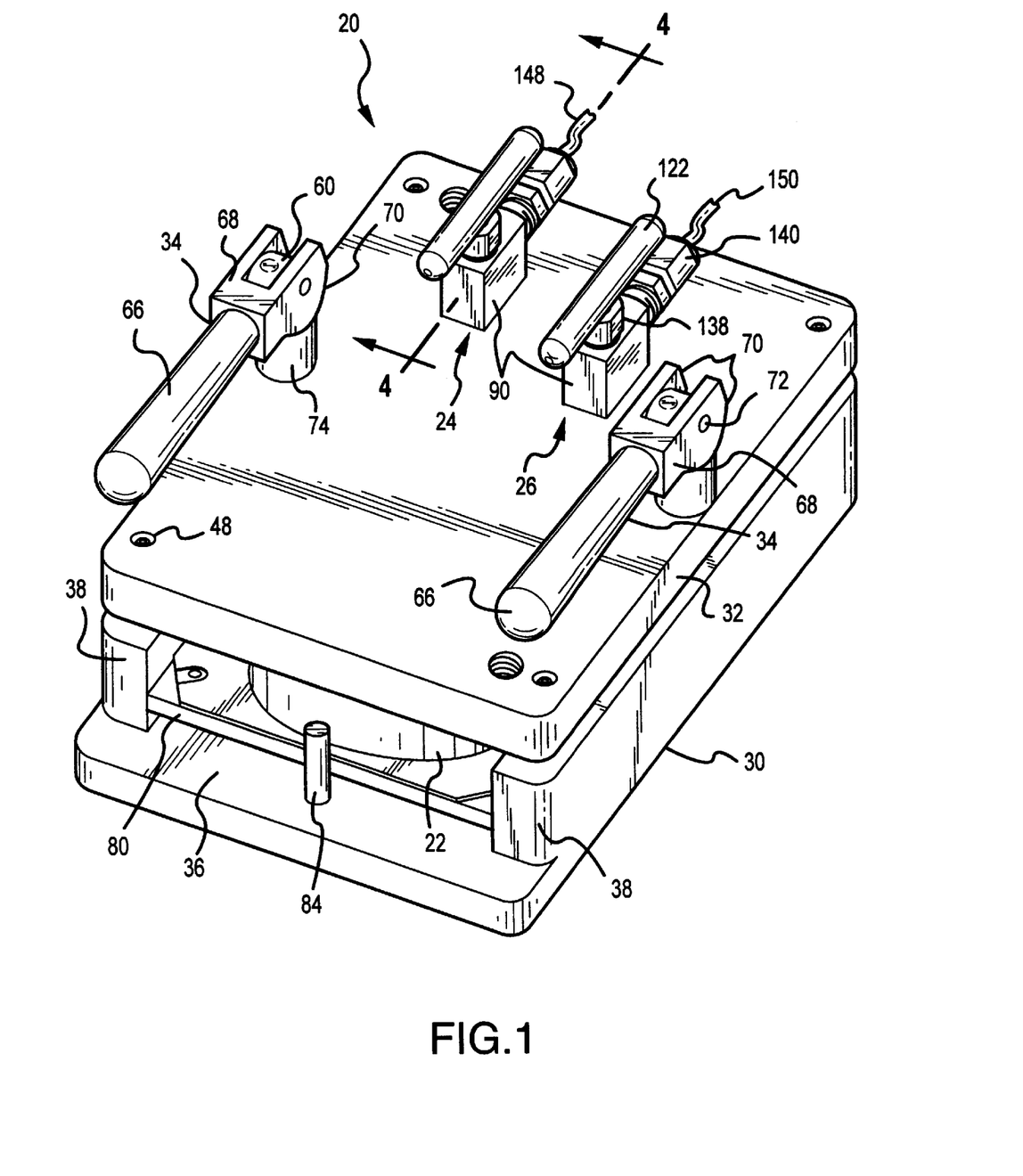
FIG. 1 is an isometric view of a disc drive contained within a disc drive outgassing apparatus in accordance with a preferred embodiment of the present invention.

FIG. 1 illustrates a preferred embodiment of a disc drive outgassing apparatus 20 of the present invention. The disc drive outgassing apparatus 20 is adapted to accommodate a disc drive 22 as shown in FIG. 1. Once the disc drive 22 is positioned within the disc drive outgassing apparatus 20 as shown, inflow and outflow valves 24 and 26, respectively, are operated to puncture the drive 22 in two separate places and create a flow path through the drive. A flow of inert gas is then used to purge outgassed compounds from the interior of the disc drive 22 over the course of a predetermined test period. These collected compounds are then analyzed to determine the composition and quantity of the compounds that are outgassed under normal operating conditions of the disc drive 22. Details of the apparatus 20 and the testing system are described below.

The disc drive outgassing apparatus 20 includes a base 30 (best shown in FIG. 2) and a top plate 32 attached to the base 30 by clamps 34. The base 30 is includes a base plate 36 and two opposing side rails 38 extending upwardly from the base plate 36. The base 30 is preferably formed from aluminum and the base plate 36 and side rails 38 are preferably machined from a single piece of aluminum. Alternatively, the base plate 36 and side rails 38 could be formed separately and then attached together.

A top surface 40 (FIG. 2) of the base plate 36 between the rails 38 is sufficiently large in both length and width to accommodate the disc drive 20. Similarly, the height of the rails 38 is approximately equal to the height of the disc drive 22, although in the preferred embodiment the height of the rails 38 is slightly less than the height of the disc drive 22 as described below. The exact dimensions of the disc drive outgassing apparatus 20 are not provided as one skilled in the art may vary these dimensions to accommodate different size disc drives.

Figure 2:
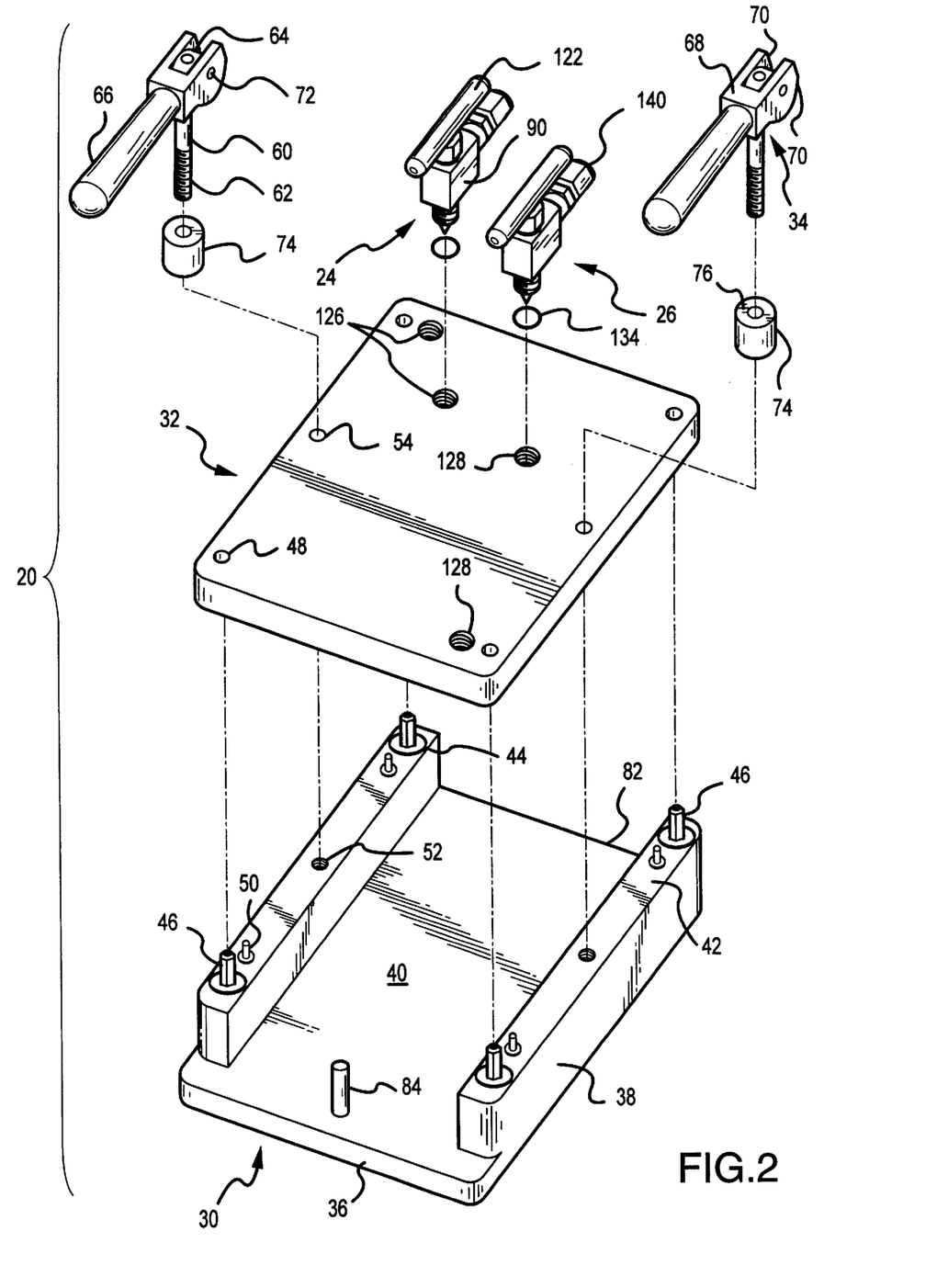
FIG. 2 is an exploded view of the disc drive outgassing apparatus shown in FIG. 1.

An upper surface 42 (FIG. 2) of each rail 38 includes threaded holes (not shown) at each end for receiving bushings 44. Each bushing 44 includes a vertical post 46 extending upward from the bushing as shown in FIG. 2. The vertical posts 46 are thus arrayed at the corners of the base 30 and are aligned with holes 48 formed through the corners of the top plate 32. The upper surface 42 of each rail 38 also preferably includes a pair of spring-loaded pins 50, with each pin 50 preferably positioned adjacent one of the posts 46. The spring-loaded pins 50 are also preferably secured within openings (not shown) formed within the upper surface 42 of the rails 38. Each pin 50 is biased into a vertically upward or extended position as shown in FIG. 2. However, each spring-loaded pin 50 can be forced downward into a retracted position by a force which exceeds the internal spring force of the pin. Each rail 38 also includes a threaded opening 52 positioned substantially at a midpoint along the upper surface 42 of the rail. The threaded openings 52 in the rails 38 are preferably aligned with openings 54 formed through the top plate 32 rail for attachment of the clamps 34, as described below.

The top plate 32 is preferably attached for limited vertical movement relative to the base 30 by placing the top plate 32 atop the rails 38 so that the posts 46 extend through the holes 48 in the top plate 32. In this manner, a bottom surface 56 of the top plate preferably contacts each of the spring-loaded pins 50 so that the pins 50 hold the top plate 32 suspended above the upper surface 42 of the rails 38. In a preferred embodiment, the spring-loaded pins 50 maintain the top plate 32 suspended above the base plate 36 a sufficient distance to allow the disc drive 22 to be inserted between the base plate 36 and the bottom surface 56 of the top plate 32. Therefore, while the height of the rails 38 is preferably less than the height of the disc drive 22 as described above, the additional height added by the spring-loaded pins 50 provides the necessary clearance to insert the disc drive 22 within the apparatus 20, as described below.

Although the top plate 32 is supported on the spring-loaded pins 50 and is free to move vertically relative to the base posts 46, the clamps 34 act to generally limit the movement of the top plate 32 and to prevent the top plate 32 from being unintentionally removed from the base 30. The clamps 34 also serve to retain the disc drive 22 within the disc drive outgassing apparatus 20.

Each clamp 34 preferably comprises an eyebolt 60 (FIG. 2) having a threaded end 62 which extends through the opening 54 in the top plate 32 for secure attachment within the threaded hole 52 in the base rail 38. A head 64 of the eyebolt 60 thus extends above the top plate 32 for connection to a clamp handle 66 as shown in FIG. 2. The clamp handle 66 includes a split cam portion 68 at one end defining two separate cams 70 spaced laterally apart from one another. The two cams 70 of the split cam portion 68 preferably fit about the head 64 of the eyebolt 60 so that a pivot pin 72 extending between the opposing cams 70 passes through an opening or "eye" (not shown) in the head 64 of the eyebolt 60. In this manner, the split cam portion 68 and the attached handle 66 may pivot about the head 64 of the eyebolt 60.

A clamp spacer 74 (FIGS. 1 and 2) is preferably placed between the top plate 32 and the split cam portion 68 of each clamp 34 to provide a bearing surface 76 for the cams 70. The head 64 of the eyebolt 60 is preferably positioned a predetermined distance above the bearing surface 76 so that in a first, "unclamped" position the cams 70 do not bear against the surface 76 of the spacers 74. In this unclamped position, the top plate 32 is preferably supported above the side rails 38 by the spring-loaded pins 50 to allow the disc drive 22 to be inserted between the top plate 32 and the base plate 36 of the base 30.

A rear end 80 (FIG. 1) of the disc drive 22 is preferably inserted within a front end 82 of the apparatus 20 and is slid rearward until the rear end 80 of the drive 22 contacts a stop 84 fixed to the base plate 36 as shown in FIG. 1. The stop 84, together with the overall dimensions of the apparatus 20, ensures that the disc drive 22 is properly positioned with respect to the valves 24 and 26, as described below. Once the disc drive 22 is positioned within the apparatus 20, each handle 66 is pivoted about the axis of the pin 72 so that the cams 70 of the split cam portion 68 engage the surface 76 of the clamp spacer 74 and drive the top plate 32 downward against the force of the spring-loaded pins 50. The handles 66 are thus pivoted from the unclamped position described above to a clamped position as shown in FIG. 1 where the top plate 32 and the valves 24 and 26 are lowered into contact with a top cover 88 (FIGS. 4 and 5) of the disc drive 22 to secure the drive 22 within the apparatus 20. The top cover 88 is typically formed from aluminum or stainless steel to protect the components within the drive 22.

Once the disc drive 22 is secured or clamped between the top plate 32 and the base 30 of the apparatus 20, the valves 24 and 26 are actuated to pierce the top cover 88 of the disc drive prior to conducting the outgassing test. The valves 24 and 26 are precisely positioned on the top plate 32 to ensure that the act of piercing the top cover 88 will not damage any vital components of the drive 22, as described in greater detail below.

Figure 3:
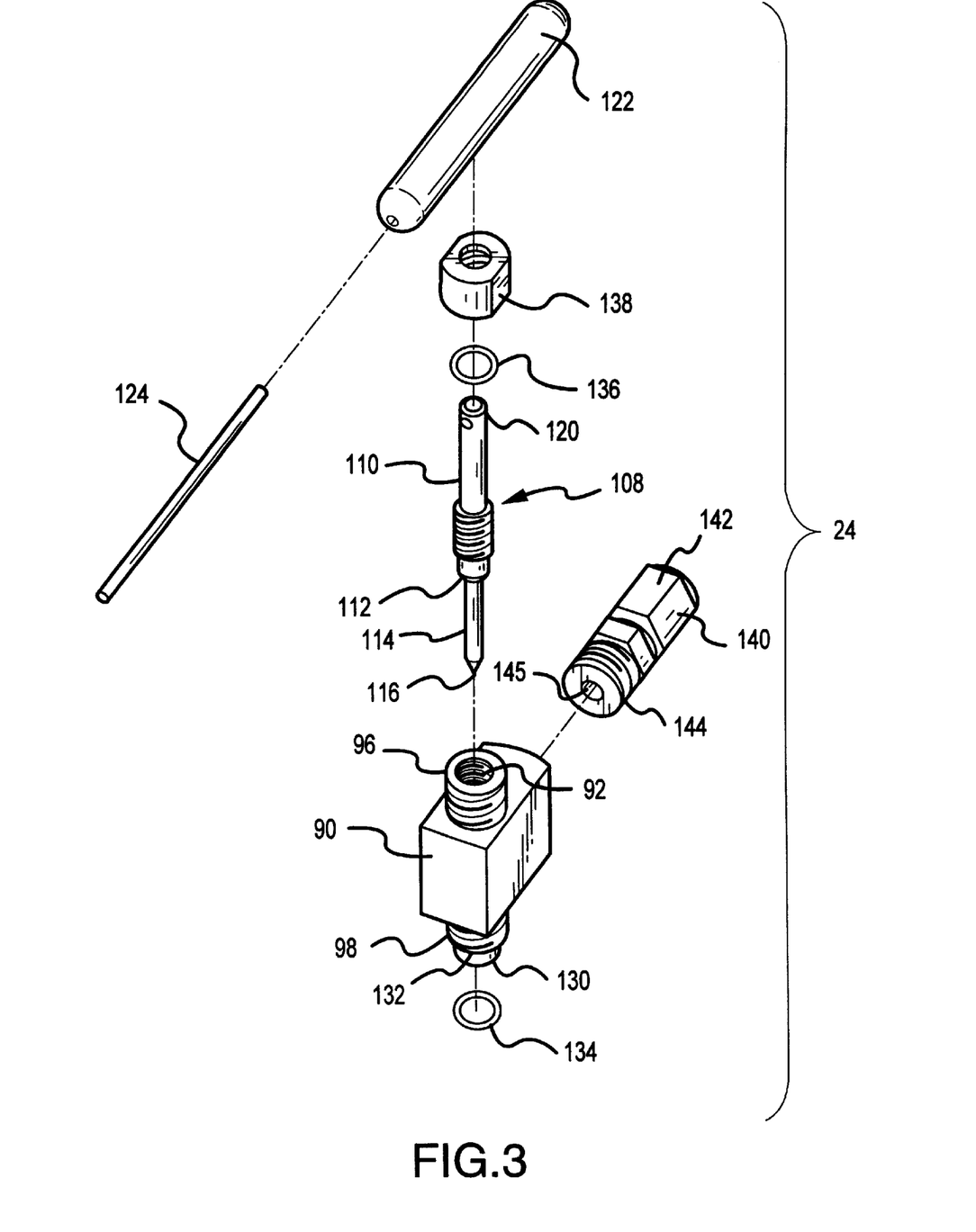
FIG. 3 is an exploded view of a valve and connector of the disc drive outgassing apparatus shown in FIG. 1.
Figure 4:
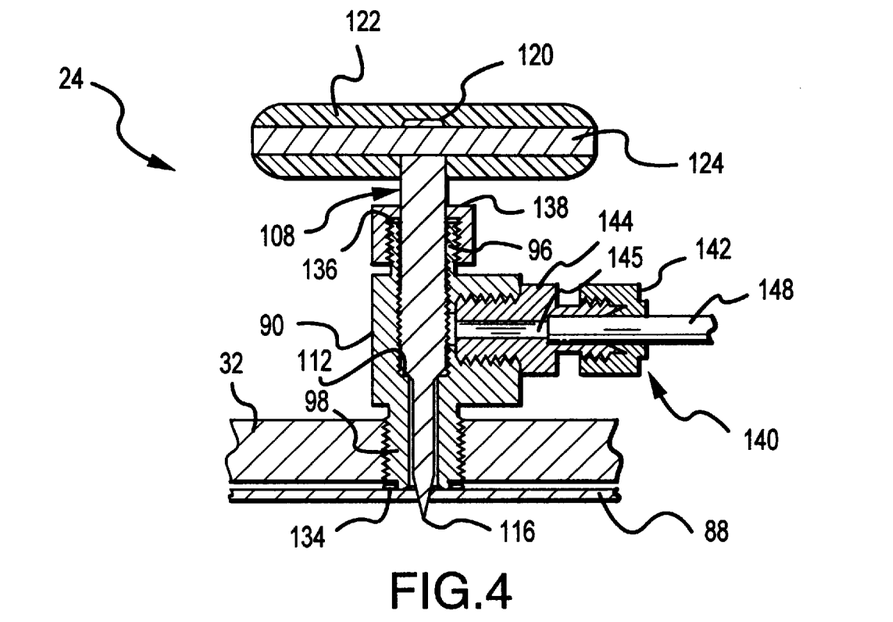
FIG. 4 is a section view taken substantially along the line 4—4 in FIG. 1 illustrating a needle plunger of the valve in an extended position.
Figure 5:
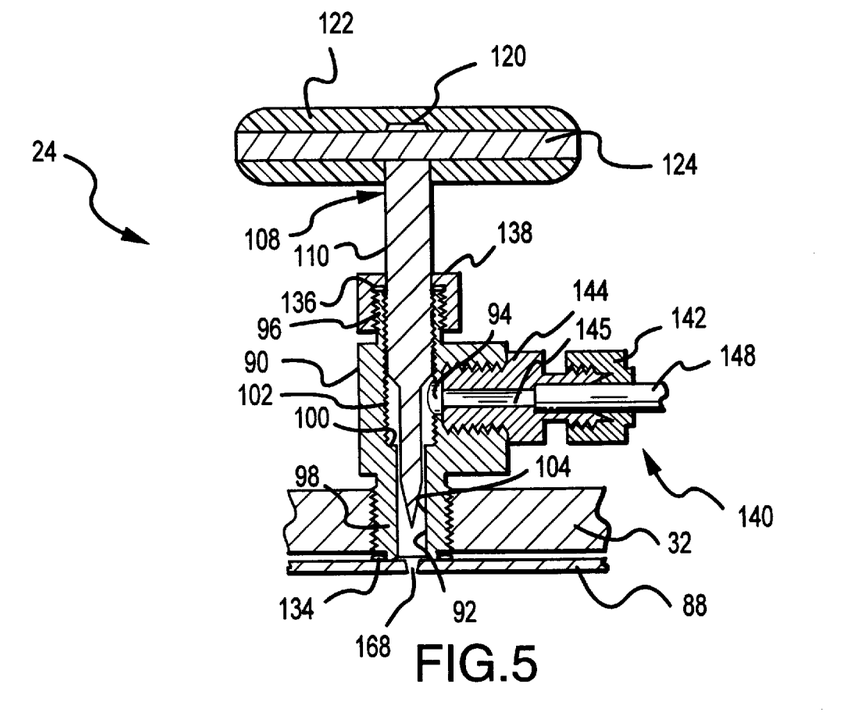
FIG. 5 is a section view similar to FIG. 4 illustrating the needle plunger of the valve in a retracted position.

The valves 24 and 26 are preferably identical to one another, and one of the valves (for example inflow valve 24) is described in detail with respect to FIGS. 3–5. The valve 24 includes a valve body 90 defining a vertical bore 92 and a horizontal bore 94 which intersects the vertical bore 92 to define a flow path through the valve body 90. The valve body 90 further includes upper and lower cylindrical portions 96 and 98, respectively, whereby the vertical bore 92 extends from the top of the upper cylindrical portion 96 to the bottom of the lower cylindrical portion 98. The vertical bore 92 preferably narrows to form an annular rim 100 (FIGS. 4 and 5) at a point below the level of the horizontal bore 94. An upper portion 102 of the vertical bore 92 above the rim 100 is preferably threaded, while a lower, narrower portion 104 is not threaded along the interior surface of the bore 92.

The vertical bore 92 of the valve body 90 is thus adapted to receive a needle plunger 108 as shown in FIGS. 3–5. The needle plunger 108 comprises an upper cylindrical body 110 which narrows at shoulder 112 (FIGS. 4 and 5) to form a shaft 114 with a sharpened tip 116 at its end. The needle plunger 108 is preferably formed from a hardened stainless steel to provide the sharpened tip 116 with sufficient strength to penetrate a number of steel or aluminum top covers 88 over the life of the apparatus 20. The upper cylindrical body 110 is preferably threaded to engage the threaded upper portion 102 of the vertical bore 92 as shown in FIGS. 4 and 5. Additionally, a top end 120 of the cylindrical body 110 preferably fits within the base of a handle 122. The top end 120 also includes a horizontal hole for receiving a rod 124 which passes through the length of the handle 122. The rod 124 thus provides torque for turning the needle plunger 108 within the valve body 90 and prevents the handle 122 from spinning about the top end 120 of the cylindrical body 110. In this manner, the needle plunger 108 may be inserted into the top of the valve body 90 and rotated via the handle 122 until the shoulder 112 of the needle plunger 108 contacts the annular rim 100 within the vertical bore 92, as shown in FIG. 4. FIG. 4 thus defines a fully extended position of the needle plunger 108 where the sharpened point 116 extends below the lower cylindrical portion 98. The handle 122 may also be turned the opposite direction to raise the point 116 and substantially withdraw the shaft 114 from the lower portion 104 of the vertical bore 92, as shown in FIG. 5. FIG. 5 thus defines a fully retracted position of the needle plunger 108 that provides fluid communication between the vertical and horizontal bores 92 and 94, as described above.

The valve body 90 is preferably attached to the top plate 32 of the apparatus 20 by screwing the threaded, lower cylindrical portion 98 into a threaded opening formed in the top plate 32. Separate openings 126 and 128 (FIG. 2) are formed in the top plate 32 for the inflow and outflow valves 24 and 26, respectively. The position of the openings 126 and 128 is carefully determined to prevent damage to the disc drive 22 when the valve points 116 puncture the top cover 88 of the drive 22 as described above. Additionally, the top plate 32 may include multiple openings 126 and 128 (FIGS. 1 and 2) so that the same apparatus 20 may be used with different disc drives 22 by simply moving the valves 24 and 26 between the different openings 126 and 128, respectively.

The lower cylindrical portion 98 of the valve body 90 preferably has a length slightly greater than the thickness of the top plate 32 so that a bottom end 130 (FIG. 3) of the cylindrical portion 98 extends slightly below the bottom surface 56 of the top plate 32 as shown in FIGS. 4 and 5. In this manner, the bottom end 130 of the lower cylindrical portion 98 of the valves 24 and 26 contacts the top cover 88 of the disc drive 22 when the clamps 34 are activated to lower the top plate 32 as described above. The bottom end 130 is preferably undercut to form an annular rim 132 (FIG. 3) for retaining an o-ring 134 (FIG. 3). The o-ring 134, preferably made from an inert material such as Viton rubber, helps to provide a hermetic seal between the valve body 90 and the top cover 88 of the disc drive 22 once the disc drive 22 is clamped within the apparatus 20. Alternatively, a septa (not shown) may be used in place of the o-ring 134 to cover the bottom end 130 of the cylindrical portion 98. The septa would provide a seal between the valve body 90 and the top cover 88 of the disc drive 22 and would be easily penetrated by the valve point 116 to allow gas flow between the drive 22 and the valve body 90. Another o-ring 136 (FIG. 3) is preferably contained within a threaded valve cap 138 which, in turn, is preferably attached to the upper cylindrical portion 96 of the valve body 90 as shown in FIGS. 3–5. The valve cap 138 and o-ring 136 act to seal the upper portion 102 of the vertical bore 92 to prevent leakage or contamination of the flow path through the valve body 90.

The horizontal bore 94 of the valve body 90 preferably widens to form a threaded port for receiving a tubing connector 140 such as the Swagelok™ connector best shown in FIGS. 3–5. Swagelok™ tubing connectors 140 preferably include a connector portion 142 for receiving an end of a gas line and a threaded base 144 for securing the connector 140 to a gas port. The connector portion 142 and the threaded base 144 of the connector 140 together define an interior passage 145 in fluid communication with the horizontal bore 94. Swagelok™ tubing connectors are well known to those skilled in the art.

Figure 6:
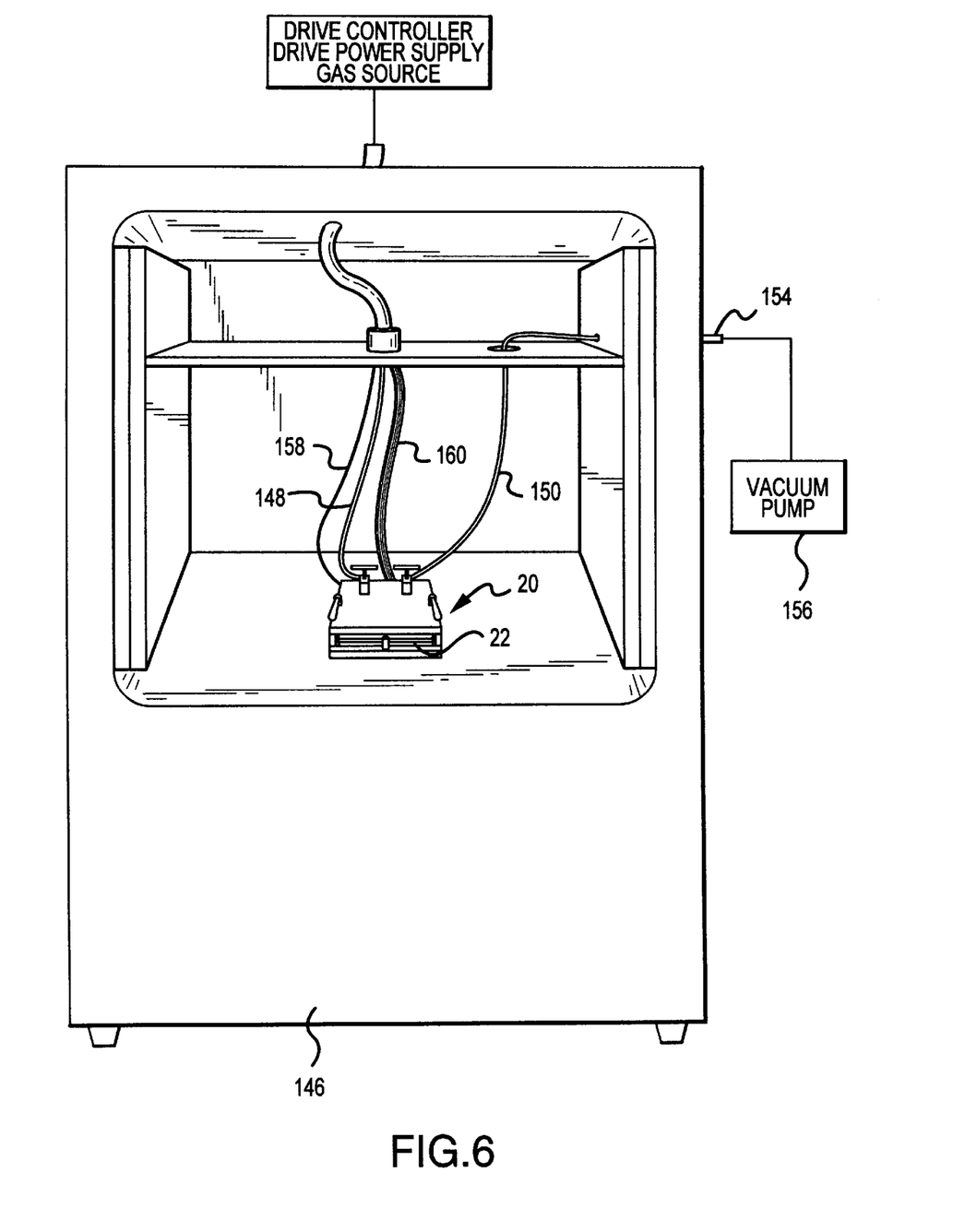
FIG. 6 is a perspective view of an oven containing the disc drive outgassing apparatus and disc drive shown in FIG. 1 together with gas inflow and outflow lines as well as disc drive controller and power supply cables extending outside of the oven.
Figure 7:
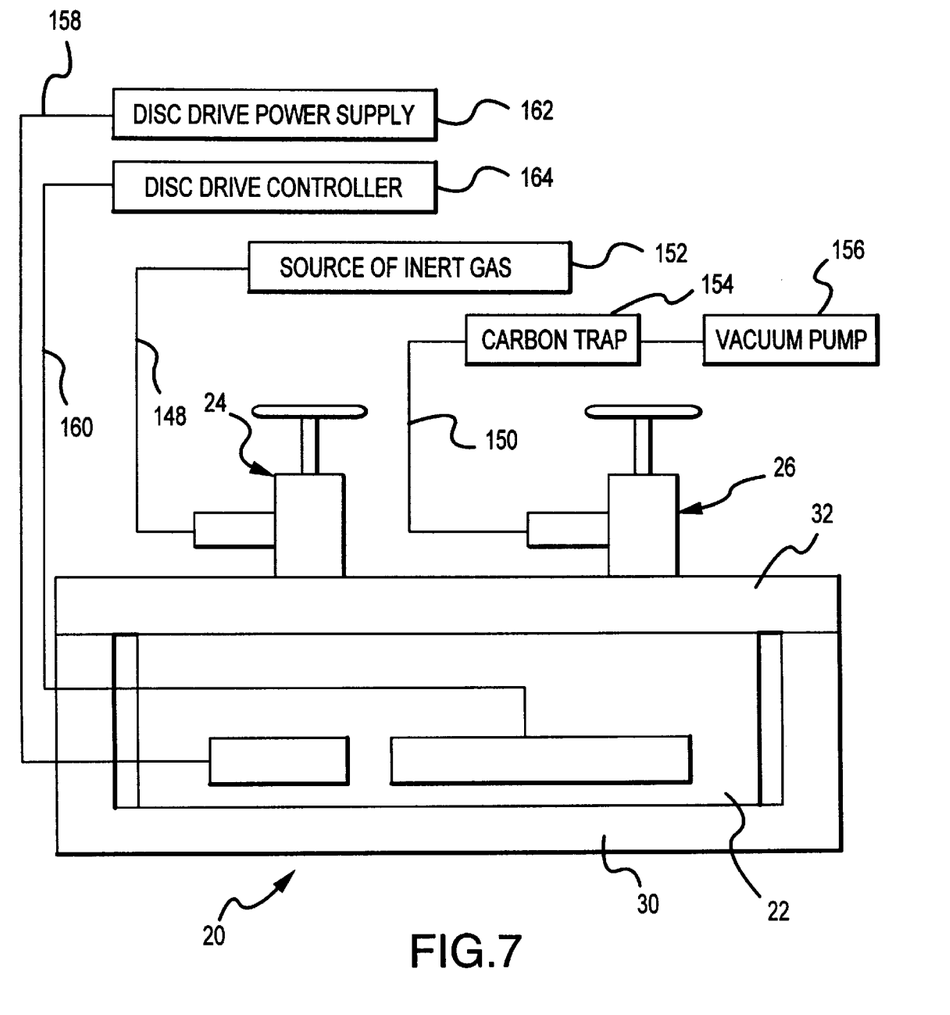
FIG. 7 is a schematic view of the disc drive outgassing apparatus and the disc drive shown in FIGS. 1 and 6, further illustrating the system for testing the disc drive in accordance with a preferred embodiment of the present invention.

A system for testing a disc drive 22 using the preferred embodiment of the disc drive outgassing apparatus 20 of the present invention is shown in FIGS. 6 and 7. Once the drive 22 is loaded and clamped within the apparatus 20 as shown in FIG. 1, the entire apparatus 20 is preferably placed within an oven 146 as shown in FIG. 6 to provide an elevated temperature for testing the drive 22. Gas inflow and outflow lines 148 and 150 (FIG. 6) are then preferably attached to the connectors 140 of the inflow and outflow valves 24 and 26, respectively. The gas inflow line 148 is connected to a source of inert gas 152 (FIG. 7) preferably positioned outside of the oven 146. The gas outflow line 150 also extends outside of the oven 146 where it connects to a first end of a trap 154 on the exterior of the oven 146. The trap 154 preferably comprises a cylindrical tube which is packed with activated carbon or other similar absorbents that bond with outgassed compounds while allowing the inert gas to pass through the trap 154. A second end of the trap 154 downstream from the outflow line 150 is preferably connected to a vacuum pump 156 for reasons described in greater detail below. Additionally, the preferred embodiment of the testing system includes cables 158 and 160 (FIG. 6) for connecting the disc drive 22 to a power supply 162 and a disc drive controller 164 (FIG. 7) positioned external to the oven 146. The power supply 162 and controller 164 allow for operation of the drive 22 during the course of the test, as described below.

Once connected as shown in FIGS. 6 and 7, the valve handles 122 are preferably rotated to lower the needle plungers 108 from their fully retracted position (FIG. 5) to their fully extended position (FIG. 4) so that the points 116 of each valve 24 and 26 pierce the top cover 88 and form separate inflow and outflow openings 168 (FIG. 5) in the disc drive. After piercing the top cover 88, the handles 122 are rotated in an opposite direction to return the needle plungers 108 to their fully retracted position (FIG. 5) and allow gas to flow freely through the openings 168, thereby defining a flow path between the inflow and outflow lines 148 and 150 through the interior of the disc drive 22. The o-rings 134 surround the openings 168 to prevent gas leakage into or out of the interior of the disc drive 22, as described above.

The outgassing test is initiated by directing a flow of inert gas from the source 152 through the inflow line 148 and into the interior of the disc drive 22. The inert gas mixes with any compounds which have been outgassed within the confines of the disc drive 22 and carries those outgassed compounds through the outflow line 150 to the trap 154. As described above, the positions of the valves 24 and 26 in the top plate 32 are calculated to prevent damaging any components of the disc drive 22 when the valve points 116 penetrate the top cover 88 of the drive 22. However, the positions of the valves 24 and 26 (and thus the positions of the inflow and outflow openings 168) are also calculated to provide for adequate gas exchange within the disc drive 22 to ensure that substantially all of the outgassed compounds are purged from the interior of the drive 22 over the course of the test.

Although the trap 154 captures the outgassed compounds, the inert gas passes through the trap 154 and on to the vacuum pump 156 where it is harmlessly discharged to the atmosphere. The vacuum pump 156 is required due to the fact that conventional disc drives 22 are not typically sealed air tight. Indeed, most conventional disc drives include a breather hole extending through the drive case to allow for equalization of the air pressure inside and outside of the drive. While absorbents and filters (not shown) are typically attached to the breather hole within the drive 22 to prevent chemical compounds or other impurities in the ambient air from contaminating the interior of the drive, the vacuum pump 156 provides a lower than ambient pressure at the exit of the trap 154 to minimize or prevent any extraneous exchange of gas during the course of the test. Additionally, in the preferred embodiment, the vacuum pump 156 also reduces the gas flow rate through the outflow line 150 and the trap 154 (e.g., a gas inflow rate through the line 148 of 53 milliliters/minute and a gas outflow rate of 50 milliliters/minute) to create a positive pressure within the drive 22 that prevents drawing contaminants into the drive during the test.

In order to convey substantially all of the outgassed compounds to the trap 154, and due to the tendency of such compounds to cling to non-inert materials (particularly at elevated temperatures), the outflow line 150 is preferably formed from an inert material such as Teflon. Similarly, in one embodiment, the inflow line 148 may also be formed of Teflon. However, since the carrier gas passing through the inflow line 148 is an inert gas (preferably grade 5 nitrogen having a purity of 99.999%), a Teflon inflow line 148 is not required. Thus, an alternative embodiment of the inflow line 148 may be formed from stainless steel or other alternative materials since the inflow line 148 will not be exposed to the heated compounds outgassed from the disc drive 22. The valves 24 and 26, as well as the Swagelok# connectors 140, are also preferably made from stainless steel to minimize or prevent contamination of the test results due to contact between the outflow valve 26 and the outgassed compounds.

To further increase the accuracy of the whole drive outgassing test, it is desirable to not only power up and spin the disc platters (not shown) within the drive 22, but rather to operate the drive 22 in a manner which is truly representative of how the drive would be operated when attached to a computer (not shown). Thus, in addition to the power supply 162 and cable 158, the preferred testing system of the present invention includes the disc drive controller 164 and ribbon cable 160 as shown in FIGS. 6 and 7. The controller 164 is preferably programmed to perform scanning and seeking operations as well as reading and writing operations as would occur during normal operation of the drive 22. Furthermore, the duration of the test is approximately four hours and the temperature of the oven 146 is approximately 70 degrees Celsius under the preferred test conditions. These test conditions, combined with representative drive operations performed by the controller 164 during the course of the test, provide extremely accurate outgassing results such as would be seen in a disc drive 22 under actual operating conditions.

At the conclusion of the test, the contents of the trap 154 are analyzed with standard equipment such as a gas chromatograph and a mass spectrometer to determine the composition of the outgassed chemicals and compounds. These results can then be compared to an overall outgassing budget to determine if one or more chemical compounds exceed a maximum tolerance previously identified for that particular compound. Additionally, the results of the whole drive outgassing test can be compared to prior outgassing test results for individual drive components. For example, if the whole drive outgassing test determines there is excessive production of a certain type of chemical compound, the prior component tests may be reviewed to determine which component within the disc drive is most likely to produce that particular compound so that remedial steps may be taken (e.g., modifying the offending component or changing suppliers for that particular component).

Both the disc drive outgassing apparatus 20 and the test system utilized with the apparatus 20 represent a vast improvement over prior art systems for testing the compounds outgassed by an entire disc drive. Such prior art systems typically require the replacement of the original drive top cover 88 with a modified cover having built-in inlet and outlet ports for purging the outgassed compounds. However, the use of a modified top cover, together with the process of removing the original top cover and installing the modified top cover, typically introduces many potential sources for error in the test results. Furthermore, it is often difficult or impossible to operate the disc drive in the above described manner when the original top cover has been removed and replaced with a modified cover. Thus, the present invention produces outgassing test results which are accurate, repeatable and truly representative of the results which one would expect under actual operating conditions.

Additionally, the disc drive outgassing apparatus 20 of the present invention is simple to use and is much faster and efficient than prior art testing systems that require disassembling the original drive and then installing a modified top cover. Indeed, a disc drive 22 can be loaded into the disc drive outgassing apparatus 20 of the present invention in a matter of seconds and the valves 24 and 26 can be quickly operated to puncture the original top cover 88 and form the flow path through the drive 22 for the test. Thus, the present invention provides for increases in the accuracy of the test results with a simultaneous reduction in amount of work and time required to perform the test. Furthermore, the disc drive outgassing apparatus 20 of the present invention is highly portable, thereby allowing testing of a disc drive 22 under any conceivable condition. For example, the apparatus 20 may be placed within a freezer or within a pressure chamber to test the drive 22 under different extremes of temperature and ambient pressure.

In summary, the preferred embodiment exemplary of the invention and disclosed herein is directed to an apparatus (such as 20) for directing a flow of gas through an interior of a disc drive (such as 22). The apparatus includes a base (such as 30) for receiving the disc drive and a top plate (such as 32) operatively connected to the base to move between a first position separated from the base for receiving the disc drive and a second position adjacent the base. Two valves (such as 24 and 26) attached to the top plate (such as 32) contact an outer cover (such as 88) of the disc drive (such as 22) when the top plate is moved to the second position. Each valve (such as 22 and 24) includes a needle plunger (such as 108) for penetrating the outer cover (such as 88) of the disc drive (such as 22) to create a flow path between the valves (such as 22 and 24) and the interior of the disc drive.

In another preferred embodiment of the present invention, the base (such as 30) includes a number of posts (such as 46) extending vertically upward, and the top plate (such as 32) includes a number of openings (such as 48) aligned to receive the posts (such as 46) for maintaining alignment of the top plate (such as 32) and the base (such as 30) as the top plate moves between the first and second positions.

In another preferred embodiment of the present invention, the base (such as 30) further includes a number of spring-loaded pins (such as 50) for contacting the top plate (such as 32) and biasing the top plate into the first position.

In another preferred embodiment of the present invention, a clamp (such as 34) is connected to both the base (such as 30) and the top plate (such as 32) to move the top plate (such as 32) from the first position to the second position against the bias of the spring-loaded pins (such as 50).

In another preferred embodiment of the present invention, the clamp (such as 34) includes a bolt (such as 60) fixed to the base (such as 30) and extending upward from the base through an opening (such as 54) in the top plate (such as 32). A cam (such as 68) pivotably connected to the bolt (such as 60) above the top plate (such as 32) is rotated by a handle (such as 66) to contact the top plate (such as 32) and force the top plate downward to the second position.

In another preferred embodiment of the present invention, the valves (such as 24 and 26) each include a valve body (such as 90) having a lower portion (such as 98) secured within an opening (such as 126 and 128) defined in the top plate (such as 32). A seal (such as 134) attached to the lower portion (such as 98) of the valve body (such as 90) contacts the outer cover (such as 88) of the disc drive (such as 22) when the top plate (such as 32) is moved to the second position.

In another preferred embodiment of the present invention, the valve body (such as 90) defines a bore (such as 92) extending the length of the valve body (such as 90), and the needle plunger (such as 108) is threaded to move between an extended position and a retracted position within the bore (such as 92). The needle plunger (such as 108) includes a pointed end (116) for penetrating the outer cover (such as 88) of the disc drive (such as 22) and forming an opening (such as 168) when the needle plunger is moved to the extended position. The seal (such as 134) surrounds the opening (such as 168) to prevent leakage into or out of the interior of the disc drive (such as 22).

In another preferred embodiment of the present invention, a tubing connector (such as 140) is attached to each valve (such as 24 and 26). The tubing connector (such as 140) defines an interior passage (such as 145) in fluid communication with the bore (such as 92).

In another preferred embodiment of the present invention, a handle (such as 122) is attached to a top end (such as 120) of the needle plunger (such as 108) for rotating the needle plunger within the bore (such as 92) to move the needle plunger between the extended and retracted positions. A valve cap (such as 138) is attached to an upper end (such as 96) of the valve body (such as 90) to seal an upper portion (such as 102) of the valve bore (such as 92).

A further preferred embodiment of the present invention includes a system for collecting outgassed compounds from a disc drive (such as 22). The system includes a disc drive outgassing apparatus (such as 20) for penetrating an outer cover (such as 88) of the disc drive (such as 22) to form inflow and outflow openings (such as 168). Inflow and outflow valves (such as 24 and 26) are adapted to contact the disc drive (such as 22) and communicate with an interior of the disc drive through the respective inflow and outflow openings (such as 168). An inflow line (such as 148) connects a source of inert gas (such as 152) to the inflow valve (such as 24) to mix the inert gas with outgassed compounds within the interior of the disc drive (such as 22). An outflow line (such as 150) connects the outflow valve (such as 26) to a trap (such as 154) containing absorbents for bonding with non-inert chemical compounds. A vacuum pump (such as 156) connected to the trap (such as 154) draws the inert gas and the outgassed compounds through the outflow line (such as 150) to the trap (such as 154) to separate substantially all of the outgassed compounds from the inert gas.

In another preferred embodiment of the present invention, a power supply (such as 162) and a disc drive controller (such as 164) perform representative operations on the disc drive (such as 22) during the outgassing test.

In another preferred embodiment of the present invention, the disc drive outgassing apparatus (such as 20) is positioned within an oven (such as 144) to maintain the disc drive (such as 22) at a predetermined temperature during the outgassing test.

In another preferred embodiment of the present invention, the outflow line (such as 150) is formed from an inert material.

A further preferred embodiment of the present invention relates to apparatus for conducting an outgassing test of an entire disc drive (such as 22) including means for penetrating an outer cover (such as 88) of the disc drive and directing a flow of inert gas through an interior of the disc drive to remove any outgassed compounds.

It will be clear that the present invention is well adapted to attain the ends and advantages mentioned as well as those inherent therein. While a presently preferred embodiment has been described for purposes of this disclosure, numerous changes may be made which will readily suggest themselves to those skilled in the art and which are encompassed in the spirit of the invention disclosed and as defined in the appended claims.

What is claimed is:

1. A disc drive outgassing apparatus for directing a flow of gas through an interior of a disc drive to test for components outgassed from components in the disc drive, the apparatus comprising the following structure adapted to receive the disc drive during the outgassing test:

a base adapted to receive the disc drive;

a top plate operatively connected to the base to move between a first position separated from the base and a second position adjacent the base; and two valves attached to the top plate, the two valves adapted to contact the disc drive when the top plate is moved to the second position, wherein one of the two valves is adapted for connection to a supply of inert gas, and wherein each valve includes a needle plunger for penetrating an outer cover of the disc drive to create a flow path for the inert gas between the two valves through the interior of the disc drive.

2. A disc drive outgassing apparatus as defined in claim 1 wherein:

the base includes a number of posts extending vertically upward; and the top plate includes a number of openings aligned to receive the posts for maintaining alignment of the top plate and the base as the top plate moves between the first and second positions.

3. A disc drive outgassing apparatus as defined in claim 2 wherein the base further includes a number of spring-loaded pins for contacting the top plate and biasing the top plate into the first position.

4. A disc drive outgassing apparatus as defined in claim 3 further comprising:

a clamp operatively connected to both the base and the top plate to move the top plate from the first position to the second position against the bias of the spring-loaded pins.

5. A disc drive outgassing apparatus as defined in claim 4 wherein the clamp comprises:

a bolt fixed to the base and extending upward from the base through an opening defined in the top plate;

a cam pivotably connected to the bolt at a position above the top plate; and a handle connected to the cam to rotate the cam into contact with the top plate and force the top plate downward to the second position.

6. A disc drive outgassing apparatus as defined in claim 1 wherein each valve further comprises:

a valve body having a lower portion secured within an opening defined in the top plate; and a seal attached to the lower portion of the valve body, the seal adapted to contact the outer cover of the disc drive when the top plate is moved to the second position.

7. A disc drive outgassing apparatus as defined in claim 6 wherein:

the valve body further defines a bore extending between an upper end of the valve body and the lower portion of the valve body;

the needle plunger is operatively connected to move between an extended position and a retracted position within the bore, the needle plunger including a pointed end for penetrating the outer cover of the disc drive when the needle plunger is moved to the extended position; and the seal surrounds an opening formed in the outer cover once the needle plunger is moved from the extended position to the retracted position.

8. A disc drive outgassing apparatus as defined in claim 7 further comprising:
 a tubing connector attached to each valve, the tubing connector defining an interior passage in fluid communication with the bore.

9. A disc drive outgassing apparatus as defined in claim 8 wherein:
 the needle plunger includes a substantially cylindrical body having a top end extending above the upper end of the valve body and a threaded portion extending within the valve bore; and
 an upper portion of the valve bore is threaded to receive the threaded portion of the needle plunger.

10. A disc drive outgassing apparatus as defined in claim 9 further comprising:
 a handle attached to the top end of the needle plunger for rotating the needle plunger within the bore to move the needle plunger between the extended and retracted positions; and
 a valve cap attached to the upper end of the valve body to seal the upper portion of the valve bore.

11. A system disc drive during an outgassing test, the system comprising the following structure adapted to receive the disc drive during the outgassing test:
 a disc drive outgassing apparatus for penetrating an outer cover of the disc drive to form separate inflow and outflow openings, the apparatus further including inflow and outflow valves adapted to contact the disc drive and communicate with an interior of the disc drive through the respective inflow and outflow openings;
 a source of inert gas be passed thru the disc drive;
 a trap containing absorbents for bonding with non-inert chemical compounds;
 an inflow line connected between the source of inert gas and the inflow valve to mix the inert gas with outgassed compounds released within the interior of the disc drive;
 an outflow line connected between the outflow valve and the trap; and
 a vacuum pump connected to the trap to draw a mixture of the inert gas and the outgassed compounds through the outflow line to the trap to separate substantially all of the outgassed compounds from the inert gas.

12. A system as defined in claim 11 further comprising:
 a power supply for supplying power to the disc drive during the outgassing test; and
 a disc drive controller for operating the disc drive during the outgassing test.

13. A system as defined in claim 12 wherein the disc drive controller is programmed to perform seeking, scaning, reading and writing operations on the disc drive during the outgassing test.

14. A system as defined in claim 12 further comprising an oven, and wherein:
 the disc drive outgassing apparatus is positioned within the oven to maintain the disc drive at a predetermined temperature during the outgassing test;
 the trap and the vacuum pump are positioned outside of the oven; and
 the outflow line passes through an opening defined in the oven to connect the outflow valve to the trap.

15. A system as defined in claim 14 wherein the outflow line is formed from an inert material.

16. A system as defined in claim 12 wherein the disc drive outgassing apparatus further comprises:
 a base adapted to receive the disc drive; and
 a top plate operatively connected to the base to move between a first position separated from the base and a second position adjacent the base for penetrating the outer cover of the disc drive.

17. A system as defined in claim 16 wherein the inflow and outflow valves each comprise:
 a valve body having a lower portion secured within an opening defined in the top plate, the valve body defining a bore extending between an upper end of the valve body and the lower portion of the valve body; and
 a needle plunger operatively connected to move between an extended position and a retracted position within the bore, the needle plunger including a pointed end for penetrating the outer cover of the disc drive when the needle plunger is moved to the extended position.

18. A system as defined in claim 17 wherein the inflow and outflow valves further comprise a seal attached to the lower portion of the valve body, the seal adapted to contact the outer cover of the disc drive and surround the respective inflow and outflow openings.

19. Apparatus for conducting an outgassing test of an entire disc drive, the apparatus comprising the following structure adapted to receive the disc drive during the outgassing test:
 inflow and outflow valves where the inflow valve is connected to a source of inert gas and the outflow valve is connected to a trap for retaining outgassed compounds; and
 means for penetrating an outer cover of the disc drive and placing the inflow and outflow valves in fluid communication with an interior of the disc drive to direct a flow of inert gas through the interior of the disc drive to test for compounds outgassing by components within the disc drive.

* * * * *

UNITED STATES PATENT AND TRADEMARK OFFICE
CERTIFICATE OF CORRECTION

PATENT NO. : 6,205,845 B1
DATED : March 27, 2001
INVENTOR(S) : Michael Paul Dinsmore and Philip John Gooras It is certified that error appears in the above-identified patent and that said Letters Patent is hereby corrected as shown below:

Title page,
Item [57], ABSTRACT
Line 9, replace "on" with -- an --.

Column 1,
Line 19, replace "hanned" with -- harmed --.

Column 9,
Line 3, replace "#" with -- ™ --.

Column 13,
Line 23, after "system", insert -- for conducting an outgassing test of a disc drive by collecting components outgassed by somponents within the --.
Line 33, after "gas", insert -- to --.

Signed and Sealed this

Thirtieth Day of July, 2002

Attest:

Attesting Officer

JAMES E. ROGAN
Director of the United States Patent and Trademark Office